United States Patent
Kastilan et al.

(10) Patent No.: US 11,300,573 B2
(45) Date of Patent: Apr. 12, 2022

(54) MEANS AND METHODS FOR PROTEIN QUANTIFICATION

(71) Applicant: Fraunhofer-Gesellschaft zur Förderung der angewandten Forschung e.V., Munich (DE)

(72) Inventors: Robin Kastilan, Aachen (DE); Catherine Müschen, Mönchengladbach (DE); Johannes Buyel, Erkelenz (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 30 days.

(21) Appl. No.: 16/636,306

(22) PCT Filed: Aug. 3, 2018

(86) PCT No.: PCT/EP2018/071152
§ 371 (c)(1),
(2) Date: Feb. 3, 2020

(87) PCT Pub. No.: WO2019/025597
PCT Pub. Date: Feb. 7, 2019

(65) Prior Publication Data
US 2021/0164988 A1    Jun. 3, 2021

(30) Foreign Application Priority Data

Aug. 3, 2017 (EP) .................................. 17184690

(51) Int. Cl.
*G01N 33/68* (2006.01)
*G01N 21/78* (2006.01)

(52) U.S. Cl.
CPC ..... *G01N 33/6827* (2013.01); *G01N 33/6833* (2013.01); *G01N 21/78* (2013.01)

(58) Field of Classification Search
CPC ............... G01N 33/68; G01N 33/6803; G01N 33/6827; G01N 33/6833; G01N 33/6839; G01N 21/77; G01N 21/78; Y10T 436/20; Y10T 436/200833; Y10T 436/203332; Y10T 436/25125; Y10T 436/2525

USPC ......... 436/86, 127, 128, 131, 164, 166, 175, 436/176; 422/400, 403, 407
See application file for complete search history.

(56) References Cited

U.S. PATENT DOCUMENTS

| | | | |
|---|---|---|---|
| 4,239,495 A | 12/1980 | Gindler | |
| 6,864,100 B1 * | 3/2005 | Ribbe | B01D 19/0404 422/503 |
| 6,900,058 B2 * | 5/2005 | Rannikko | G01N 21/8483 252/408.1 |
| 2004/0180444 A1 | 9/2004 | Rannikko | |
| 2009/0061522 A1 | 3/2009 | Collins | |
| 2017/0227530 A1 * | 8/2017 | Finison | G01N 33/6833 |

FOREIGN PATENT DOCUMENTS

| EP | 1 014 089 A2 | 6/2000 |
|---|---|---|
| EP | 2 031 399 A1 | 3/2009 |
| WO | WO 00/03242 A2 | 1/2000 |
| WO | WO 02/04658 A1 | 1/2002 |
| WO | WO 2013/027008 A1 | 2/2013 |

OTHER PUBLICATIONS

Edelhoch, H., Spectroscopic Determination Of Tryptophan and Tyrosine In Proteins, *Biochemistry*, vol. 6, pp. 1948-1954, 1967.
International Search Report and Written Opinion, dated Nov. 6, 2018, in International Application No. PCT/EP2018/071152.
International Preliminary Report on Patentability, dated Feb. 4, 2020, in International Application No. PCT/EP2018/071152.

* cited by examiner

*Primary Examiner* — Maureen Wallenhorst
(74) *Attorney, Agent, or Firm* — Knobbe, Martens, Olson & Bear LLP

(57) ABSTRACT

Biochemical test methods for protein quantification can include application of foam-suppressing and/or foam-destroying substances to avoid readout problems and ensure the accuracy of measurement results. One such method for determining the amount of one or more proteins in a solution includes providing at least a first solution that is known to contain or suspected of containing one or more protein(s), adding at least one foam-suppressing and/or foam-destroying substance to the first solution, resulting in a second solution, and determining the amount of the one or more protein(s) in the second solution.

14 Claims, 6 Drawing Sheets

A)

B)

Figure 2 contin.
C)
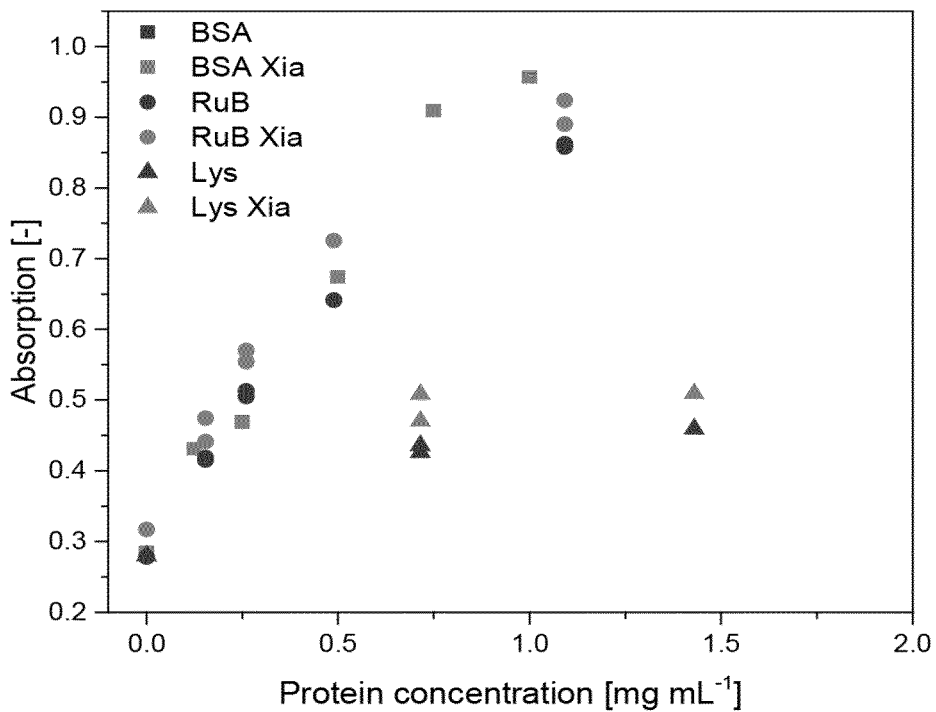
D)
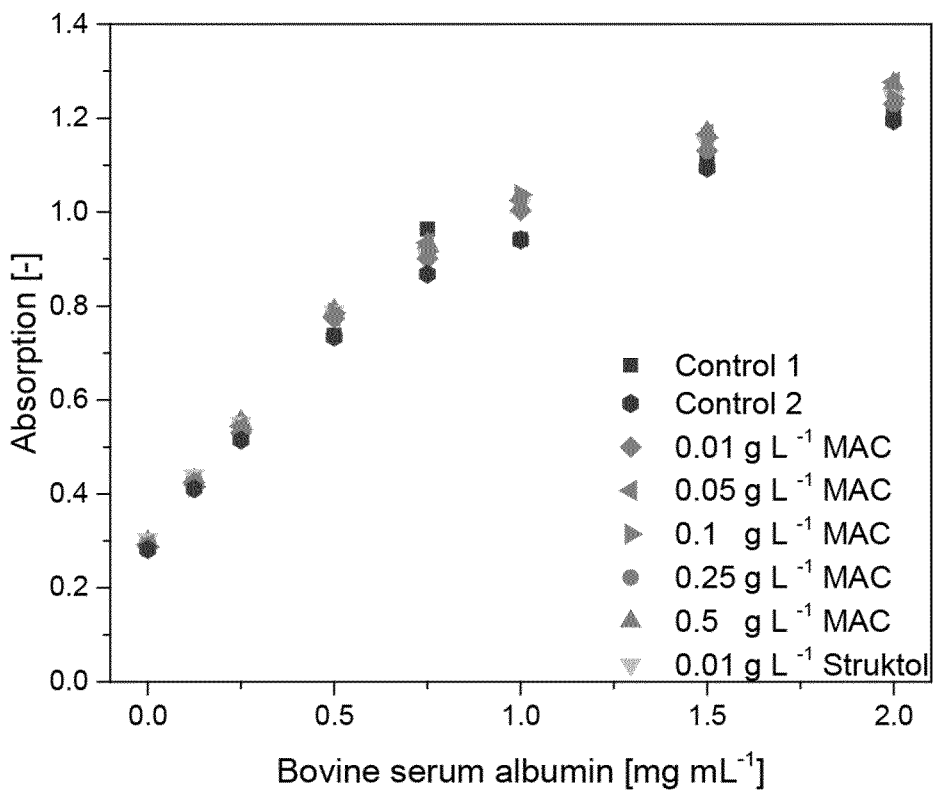

MEANS AND METHODS FOR PROTEIN QUANTIFICATION

PRIORITY AND CROSS REFERENCE TO RELATED APPLICATIONS

This application is the U.S. National Phase Application under 35 U.S.C. § 371 of International Application No. PCT/EP2018/071152, filed Aug. 3, 2018, designating the U.S. and published in English as WO 2019/025597 A1 on Feb. 7, 2019, which claims the benefit of European Application No. EP 17184690.0, filed Aug. 3, 2017. Any and all applications for which a foreign or a domestic priority is claimed is/are identified in the Application Data Sheet filed herewith and is/are hereby incorporated by reference in their entireties under 37 C.F.R. § 1.57.

FIELD

The present invention relates to biochemical test methods for protein quantification.

SUMMARY

The present invention relates to biochemical test methods for protein quantification and, in particular, to the application of foam-suppressing and/or foam-destroying substances for avoiding readout problems and ensuring the accuracy of measurement results. Specifically, the present invention pertains to a method for determining the amount of one or more proteins in a solution comprising: (a) providing at least a first solution that is known to contain or suspected of containing one or more protein(s), (b) adding at least one foam-suppressing and/or foam-destroying substance to the first solution, resulting in a second solution, (c) determining the amount of the one or more protein(s) in the second solution. Encompassed by the present invention is also the use of a foam-suppressing and/or foam-destroying substance for the quantification of the protein content in a solution.

DETAILED DESCRIPTION

Figure 1:
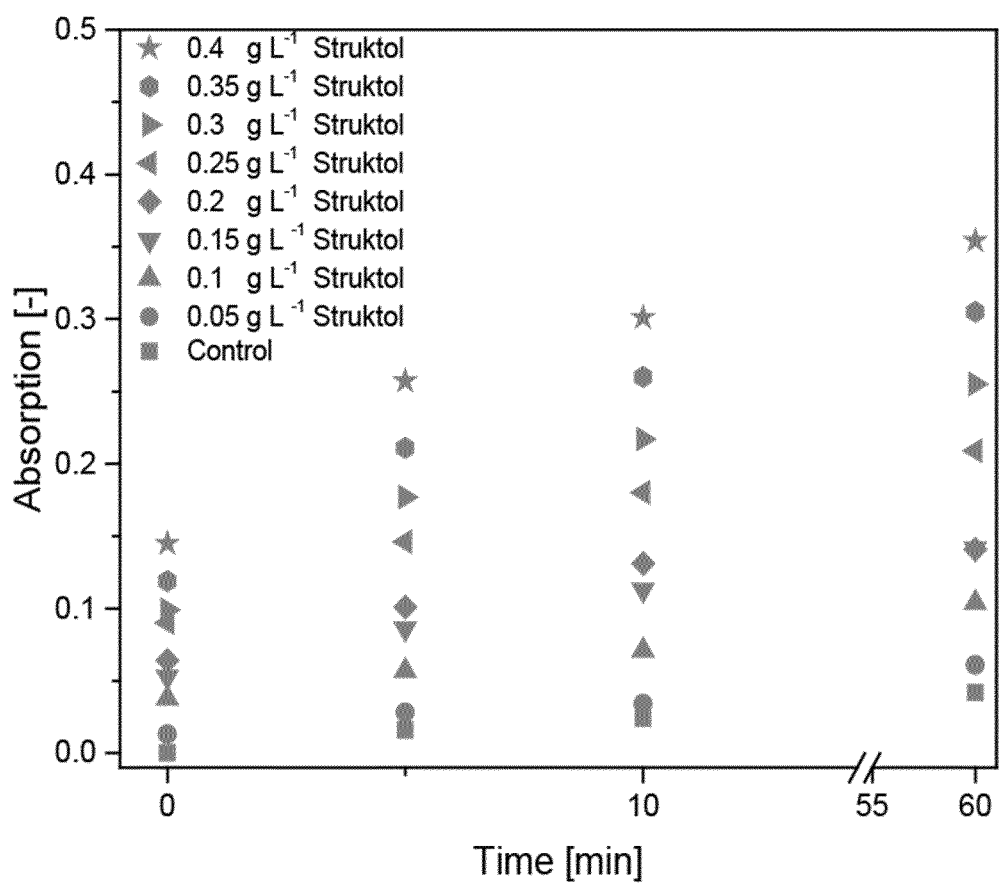
FIG. 1 shows effect of the Struktol concentration (Struktol J673) on absorption over time. As the Struktol concentration increases, the absorption increases. An increase in absorption can be observed over time, and a saturation curve can be seen at lower Struktol concentrations up to approx. 0.2 g L−1, above that the course is linear.

Most protein-containing aqueous solutions have the highest absorption at about 280 nm in the spectrophotometer, the so called UV range. This requires spectrophotometers capable of measuring in the UV range, which many, especially in a high throughput setting, cannot do. Additionally, the absorption maximum at 280 nm requires that proteins contain aromatic amino acids such as tyrosine (Y), phenylalanine (F) and/or tryptophan (W). However, not all proteins will contain these amino acids and thus cannot be measured in such assays. Therefore, so called colorimetric tests or color-turnover-based protein quantification methods, where the protein concentration is determined by means of a color-imparting reagent, have been developed. Methods such as the Bradford assay, the bicinchoninic acid (BCA) assay and the Lowry method are well known in the art.

Briefly, the Bradford assay is based on an absorbance shift of the dye Coomassie Brilliant Blue G-250 which forms blue complexes with proteins, especially by interactions with arginine residues, thereby stabilizing the blue form of the Coomassie dye. These complexes have an absorption maximum at a wavelength of 595 nm. Since the absolute level of absorption of the complexes is directly proportional to the protein concentration in the measured solution, protein quantities can be determined by reference to standard solutions, for example bovine serum albumin (BSA) solutions with known protein content. The bicinchoninic acid (BCA) assay is based on the fact that cysteine/cystine, tyrosine, tryptophan and peptide bonds reduce Cu2+ to Cu+ under appropriate conditions. Cu+ forms a deep purple color complex which absorbs around 562 nm.

The Lowry method is also a colorimetric method for the determination of protein concentrations in solutions, which is related to the biuret reaction. In the Lowry method Cu+ is oxidized back to Cu2+ by use of the so called Folin-Ciocalteu's reagent. In the first step, a copper-protein complex is formed in alkaline solution. This complex then reduces an added mixture of phosphomolybdate and phosphotungstate (Folin-Ciocalteu's reagent). Depending on the amount of proteins present, the solution becomes intensely blue. The absorption of the solution can then be measured at a wavelength of 540, 650 or 750 nm, and the protein quantities contained therein can be determined with the aid of a calibration curve.

However, all the above mentioned methods and especially the colorimetric methods are easily disturbed, for example by changes in the liquid surface of the sample. As mentioned above, in color-turnover protein assays, such as the Bradford Assay, a shift in the light absorption spectrum can be detected in the presence of proteins. The strength of light absorption can be quantified, e.g. by using a photometer, and correlates with the protein concentration being present n the solution. Typically, cuvettes are used as test vessels, which have a beam path defined in its length for the light radiated through the measuring solution.

Since the irradiation of the light takes place horizontally through the wall of the cuvettes, the surface texture of the measuring solution is irrelevant as long as the light beam passes through without being broken at the liquid surface. However, the surface is often not equally smooth. For example, due to pipetting or mixing process, bubbles or fine foam often occur that have an influence on the light adsorption and thus on the accuracy of the measurement result.

Furthermore, for high-throughput approaches often microtiter plates, for example 96-well or 384-well plates, are used. Due to the geometry of such plates, a measurement with a horizontal beam path is not possible. Instead, a vertical structure has to be used. In this case, however, bubbles or foam influence the distance of the light even more than in the case of a horizontal structure and thus may even more affect the measurement result.

Currently used methods for destroying bubbles or foam are mainly mechanical or thermal in nature and have a lot of drawbacks such as being difficult to employ on a large scale and very time-consuming. The use of mechanic means such as centrifugation of many plates is often complex, expensive and, thus, not practicable in automated liquid handling systems. Thermal means such as the heating of plates is also very time consuming and often not practicable in a high throughput approach. Moreover, means involving potentially explosive ethanol vapor may be used to destroy bubbles or foam before the measurement. However, thermal or steam-based methods place a high demand on protective devices and measures for ongoing operations and are thus not practicable for automated and parallelized measurements.

Anti-foam agents are known from processes such as wastewater treatment, paper making or fermentations. Several anti-foam agents are commercially available. These agents are capable of suppressing foam-building and/or destroying already formed foam-bubbles in various solutions. In addition, most of the known antifoam agents are non-toxic and therefore form a low safety risk.

US2004180444 is related to the measurement of blood glucose levels using a spectrophotometer and discloses a control solution comprising a predetermined amount of glucose, a hydrophobic reference dye and a surfactant. The hydrophobic reference dye preferably has a maximum absorbance of light at a wavelength in the range of between about 700 nm to about 1,100 nm so the control solutions of the invention mimic the light absorbance of whole blood. In an embodiment of the invention, the control solution further comprises an anti-foam agent. However, the use of an anti-foam agent in an automated and parallelized protein quantification assay is not disclosed nor implied.

US2009061522 relates to an automated protein analysis method, particularly for determining the protein content in various food samples, including a homogenizer for reducing protein samples to small particles. EP 2 031 399 A1 suggests to use an alcohol (e.g., ethanol) to reduce foaming However, ethanol vapor approaches are not practicable for automated and parallelized measurements and thus not for high-throughput protein quantification approaches.

As explained above, none of the currently known methods for protein quantification account for the inaccuracy of measurement results due to bubbles or foam in the sample. Especially for high throughput approaches no method is currently available that would fulfill the requirements of practicability, repeatability and reproducibility of the results. Thus, an optimized method for protein quantification, especially for parallelized and automated high throughput protein quantifications, is highly desired.

The technical problem underlying the present invention can be seen as the provision of means and methods for complying with the aforementioned needs. The technical problem is solved by the embodiments characterized in the claims and herein below.

The present invention pertains to a method for determining the amount of one or more proteins in a solution comprising:
(a) providing at least a first solution that is known to contain or suspected of containing one or more protein(s),
(b) adding at least one foam-suppressing and/or foam-destroying substance to the first solution, resulting in a second solution,
(c) determining the amount of the one or more protein(s) in the second solution.

The term "solution" as used herein refers to a mixture composed of one, two or more substances dissolved in a solvent. For example, a mixture of NaCl and water where NaCl (i.e. the solute) is dissolved in water (i.e. the solvent) is regarded as solution. The term solution encompasses aqueous solutions as well as non-aqueous solution such as alcohol extracts. An aqueous solution as used herein refers to a solution that comprises water as solvent and, preferably, retains the characteristics of water. The aqueous solution may contain several dissolved substances (solutes). All solutions that do not comprise water as the predominant solvent are considered as non-aqueous solution. Non-aqueous solutions include, for example, alcoholic extracts or concentrated acid solutions.

According to the present invention, the solution may also, preferably, be an extract. The term "extract" as used herein relates to a non-aqueous solution, preferably, to an alcoholic extract that comprises one or more protein(s). Means and methods for production of alcoholic extracts are well known to those skilled in the art. For example, proteins from plant or animal material may be extracted with ethanol, methanol, isopropyl alcohol, butanol, 2-methyl pentane, diethyl ether or acetone. In addition to the use of organic solvents such as ethanol, methanol, or acetone, solutions containing acids such acetic acid, trichloroacetic acid (TCA) or trifluoroacetic acid (TFA) can be used to generate an extract comprising one or more protein(s). According to the present invention the extract is, preferably, an ethanol and/or acetic acid extract.

It is to be understood that the words "solution", "extract", "emulsion", "liquid formulation" or similar expressions as used herein are used in a non-exclusive way and relate, preferably, to a homogeneous mixture composed of two or more substances. It is further known to those skilled in the art that a solution may have a certain appearance such as a certain color, viscosity or surface tension, depending on the solvents and solutes contained in the solution.

A "first solution" according to the present invention is a solution that is known to contain or suspected of containing one or more protein(s). Preferably, said first solution is an aqueous solution or an extract.

A "second solution" according to the present invention is a solution that is known to contain or suspected of containing one or more protein(s) (i.e. the first solution) and in addition comprises at least one foam-suppressing and/or foam-destroying substance, i.e. is a first solution according to the present invention further comprising at least one foam-suppressing and/or foam-destroying substance. According to the present invention, the foam-suppressing and/or foam-destroying substance may be added directly to the first solution or may be first added to a color-imparting reagent that then is added to the first solution as explained elsewhere herein in detail.

Preferably, the foam-suppressing and/or foam-destroying substance is added to the first solution in a concentration that is less than or equal to 0.05% (m/v). More preferably, the foam-suppressing and/or foam-destroying substance is directly added to the color-imparting reagent in a concentration of about 0.05% (m/v), so that concentration in the second solution is slightly less than 0.05% (m/v). It is envisaged that the color-imparting reagent comprising the foam-suppressing and/or foam-destroying substance can be stored for several days, weeks, months or even years at an appropriate temperature (e.g. at 4 degrees) and place (light-protected) and applied as "ready-to-use solution" when performing a color-turnover-based protein quantification method, e.g. the Bradford assay, according to the present invention.

In a further preferred embodiment of the method of the present invention, at least two foam-suppressing and/or foam-destroying substances are added to the first solution. The use of at least two foam-suppressing and/or foam-destroying substances preferably reduces the amount of each substance needed to effectively avoid bubbles. Preferably, said at least two foam-suppressing and/or foam-destroying substance are added to the first solution in a concentration that is less than or equal to 0.5 g $L^{-1}$, more preferably less than 0.5 g $L^{-1}$. More preferably, said at least two foam-suppressing and/or foam-destroying substances are selected from the group consisting of alkoxylated fatty acid esters and siloxane-based compounds, most preferably said at least two foam-suppressing and/or foam-destroying substances are Struktol J673A and Xiameter AFE 0100 or Struktol J673A and Medical Antifoam C as explained elsewhere herein. Preferably, the amount of each of Struktol J673A and Xiameter AFE 0100 or each of Struktol J673A and Medical Antifoam C can be reduced by at least 70%, at least 80%, at least 90% or more than 90%, when using both agents in combination compared to using either Struktol J673 or Xiameter AFE 0100 alone or using either Struktol J673 or Medical Antifoam C alone to effectively avoid bubble formation.

A protein as referred to herein relates to a molecule consisting of amino-acid residues joined by peptide bonds. The term encompasses larger proteins comprising 100 or more amino acids as well as shorter proteins, i.e. peptides. Peptides that typically consist of at least 20, at least 30, at least 40, at least 50 or at least 60 amino acids that are covalently linked to each other by peptide bonds, are commonly referred to as polypeptides. Molecules consisting of less than 20 amino acids covalently linked by peptide bonds are usually considered to be peptides. According to the present invention, one or more protein(s) shall be present in a solution, preferably an aqueous solution as explained elsewhere herein.

Moreover, the term protein includes natural occurring proteins as well as synthetic proteins. Natural occurring proteins relate to all proteins that naturally form part of an organism's proteome and thus can be derived from natural sources. Preferably said natural source is a microorganism, plant, animal or virus/phage. Synthetic proteins encompass all proteins that are synthetically produced. Synthetic proteins may have genetic sequences that are not seen in natural proteins. Means and methods to synthetically produce a protein with a desired amino acid sequence, e.g. an amino acid sequence that is not seen in a natural protein, are known in the art and include, for example, chemical synthesis or recombinant gene technology.

Recombinant expression of one or more protein(s) of interest is well known in the art and is typically achieved by the use of suitable expression vectors in a suitable host vector. An expression vector typically refers to a recombinant DNA molecule containing appropriate control nucleotide sequences such as promoters, enhancers, repressors, operator sequences and ribosome binding sites necessary for the expression of an operably linked nucleotide sequence in a particular host cell. Operably linked means that the nucleotide sequence is positioned relative to the control nucleotide sequences to initiate, regulate or otherwise direct transcription and translation and/or the synthesis of the desired protein molecule. The expression vector may be a self-replicating vector, such as a plasmid, and may therefore carry a replication site, or it may be a so called stable vector that integrates into a host chromosome either randomly or at a targeted site. It is also known by those skilled in the art that an expression vector may contain further sequences, for example, transcription and translation control sequences or antibiotic resistance genes that can be used as selectable marker for phenotypic selection in transformed cells.

It will be further understood by those skilled in the art that a protein can be a modified or unmodified protein. Protein modifications are well known in the art and include, for example, the addition of polyethylene glycol (PEG) or fluorescent molecules to a protein or interest. Modifications may be introduced during chemical synthesis or the recombinant expression of proteins comprising a 6xHIS tag or a fluorescent tag such as green fluorescent protein (GFP), red fluorescent protein (RFP) or yellow fluorescent protein (YFP). Recombinant proteins comprising regions derived from at least two different proteins, e.g. from albumin and GFP, are commonly also referred to as fusion proteins. In an expression vector to produce a fusion protein, the nucleotide sequence encoding the first protein of interest, e.g. albumin, is joined in frame to the nucleic acid encoding the second protein of interest, e.g. GFP, to provide for a single amino acid chain when transcription and translation occur.

The term "amount" as used herein relates to a measure of quantity. It will be understood by those skilled in the art that the term amount includes absolute as well as relative quantities. According to the present invention, the amount of the one or more protein(s) in a solution shall be determined. Means and methods to determine the amount of a protein are known in the art and include color-turnover-based protein quantification methods such as the Bradford Assay as well as non-color-turnover-based protein quantification such as the Edelhoch-Method as explained elsewhere herein. Preferably, the amount according to the present invention is the concentration of one or more protein(s) in a solution, preferably in an aqueous solution or an extract as explained elsewhere herein.

It will be understood that the terms "at least one", "one or more" as used herein or similar expressions shall indicate that a feature or element may be present once or more than once and shall typically be used only once when introducing the respective feature or element. In the following, in most cases, when referring to the respective feature or element, the expressions "at least one" or "one or more" will not be repeated, non-withstanding the fact that the respective feature or element may be present once or more than once.

Moreover, the terms "have", "comprise" or "include" as used herein or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

The terms "foam-suppressing" and "foam-destroying" substance as used herein refer to any substance capable of suppressing the formation of bubbles or foam as well as any substance capable of destroying bubbles or foam that have already built up. A foam-suppressing and/or foam-destroying substance may be present in any form including liquid formulations, powder or tabs. Formulations comprising a foam-suppressing and/or foam-destroying substance may also include further substances such as emulsifiers or stabilizers, for example polyethylene glycol (PEG). Commonly, foam-suppressing and foam-destroying substances are referred to as anti-foam agents. Anti-foam agents are well known in the art and are frequently used in processes such as wastewater treatment, paper making or fermentations. Several anti-foam agents are commercially available and include, for example, anti-foam solutions from Schill+Seilacher GmbH such as Struktol® and especially Struktol® 647, Struktol® J673 and Struktol® 673A for biotechnology and food industry applications, anti-foam solutions from Dow Corning Corp. such as 365-35% Dimethicon NF Emulsion and Medical Antifoam C, anti-foam solutions from BASF SE such as Pluronic® L61 as well as anti-foam solutions from Geo® Speciality Chemicals such as Bisomer® G30.

According to the present invention, the foam-suppressing and/or foam-destroying substance preferably comprises an alkoxylated fatty acid ester and/or a siloxane-based compound and/or methyl cellulose and/or an ethylene oxide (EO)/propylene oxide (PO) copolymer.

Alkoxylated fatty acid esters are known to those skilled in the art. Fatty acid esters are esters that result from the combination of a fatty acid and an alcohol. In general, an ester is a chemical compound derived from an organic or inorganic acid in which at least one hydroxyl (—OH) group is replaced by an Alkoxy group (—O-alkyl). For example, glycerides are fatty acid esters of glycerol. An alkoxylation is a chemical reaction that involves the addition of an epoxide to another compound. Typically, the manifestation of the alkoxylation-reaction is the ethoxylation of alcohols (ROH) where ethylene oxide ($C_2H_4O$) serves as alkoxylating agent (ROH+$C_2H_4O$ →ROCH$_2$CH$_2$OH).

Preferably, an alkoxylated fatty acid ester according to the present invention is an alkoxylated fatty acid ester on a vegetable basis. The alkoxylated fatty acid ester may be formulated as an aqueous solution or emulsion. Preferably, the alkoxylated fatty acid ester is formulated as a liquid with a density of 1000 kg/m3 (at 20 degrees) and a dynamic viscosity of 500 mPa·s (at 25 degrees). Suitable formulations of alkoxylated fatty acid esters are commercially available, for example under the brand Struktol® from Schill+Seilacher GmbH. Preferably, according to the present invention, Struktol® J673 and/or Struktol® J673A from Schill+Seilacher GmbH shall be used. According to manufacturer's data, Struktol® J673/J673A is an alkoxylated fatty acid ester on a vegetable basis with a density of 1000 kg/m3 (at 20 degrees) and a dynamic viscosity of 500 mPa·s (at 25 degrees). Struktol® J673A has been described as defoamer for fresh yeast or antifoam agent for fermentation processes while Struktol® J673 is recommended as defoamer for vegetable processing.

Siloxane-based compounds are also known to those skilled in the art. A siloxane is known as a functional group with an Si—O—Si linkage in an organosilicon compound, i.e. a compound with a carbon (C)—silicon (Si) bond. Siloxanes include oligomeric and polymeric hydrides as well as branched compounds. In branched compounds, each pair of silicon centres is separated by one oxygen atom. The siloxane functional group also termed siloxy group, $(RO)_3Si$ forms the backbone of silicones. Siloxane-based compounds include linear siloxanes such as dimethicones (poly(dimethylsiloxane)) as well as cyclic polydimethylsiloxane polymers (Cyclomethicones). As the siloxane functional group forms the backbone of silicones, polysiloxane compounds are also simply referred to as silicones or silicone polymers. Siloxane-based compounds thus include any inert, synthetic compound made up of repeating units of siloxane, which is a chain of alternating silicon atoms and oxygen atoms, frequently combined with carbon and/or hydrogen. Moreover, siloxane-based compounds may be formulated in any way e.g. as aqueous solution or emulsion. Preferably, food-grade or medical grade silicone polymers are used.

Preferably, the siloxane-based compound is dimethyl siloxane or polydimethylsiloxane. Polydimethylsiloxane, also called dimethicone, belongs to a group of polymeric organosilicon compounds that are commonly also referred to as silicones. Preferably, the polydimethylsiloxane to be used according to the present invention, is formulated as an aqueous emulsion from a polydimethylsiloxane concentrate with a final concentration of polydimethylsiloxane of at least 5%, at least 10%, at least 20%, at least 30%, at least 40%, at least 50% or at least 60%. More preferably, the final concentration of polydimethylsiloxane is about 30%. The solution or aqueous emulsion comprising a siloxane-based compounds may also comprise one or more further substances such as stabilizers, diluents or methyl ethers like methylcellulose. Most preferably, the siloxane-based compound is formulated as an emulsion containing α—(Trimethylsilyl)-ω-methylpoly[oxy(dimethylsilylen)] (also known as dimeticone silica or Simethicone USP) and methylcellulose. Preferably, said emulsion comprises 30% Dimeticon-Siliciumdioxid by mass. A respective formulation is available from Dow Corning Corp. under the name "Medical Antifoam C". A further formulation comprising polydimethylsiloxane and hydrated silica gel, also known as simethicone, is available from Dow Corning Corp. under the name "Q7-2243 LVA, SIMETHICONE USP".

About as referred to herein refers to any specific value referred to in this specification, e.g. the concentration of a siloxane-based compound of about 30% in a solution, including any variation which is within the range of +/−20%, +/−10%, +/−5%, +/−4%, +/−3%, +/−2% or +/−1%.

In a further preferred embodiment of the present invention, the siloxane-based compound or silicone polymer is formulated as a water-dilutable silicone emulsion, preferably with a silicone content of about 30%. Also, preferably said water-dilutable silicone emulsion has a pH of about 3.5. The water-dilutable silicone emulsion may also contain further substances such as Polyethylene glycol. Several suitable silicone emulsions are commercially available, for example the XIAMETER® silicone antifoam solutions from Dow Corning Corp.

Also preferably, the XIAMETER® AFE-0100 Antifoam Emulsion FG is used according to the present invention. According to manufacturer's data, the XIAMETER® AFE- 0100 Antifoam Emulsion FG is a 30% food-grade silicone emulsion with a pH of 3.5 and a nonionic emulsifier. The following ingredients may also be comprised in said emulsion: Polyethylene glycol stearate (preferably in a concentration m: >=3 to <=4), Polyethylene glycol (preferably in a concentration concentration m: >=2.9 to <=3.1), Dimethyl Siloxane reaction with Silica (preferably in a concentration concentration m: >=2.1 to <=2.2) and Octamethylcyclotetrasiloxane (preferably in a concentration concentration m: >=1.3 to <=1.4).

Methyl cellulose is a chemical compound derived from cellulose that is synthetically produced, e.g. by heating cellulose with a solution of sodium hydroxide and treating it with methyl chloride, so that the hydroxyl residues (—OH functional groups) are replaced by methoxide (—OCH$_3$ groups). Methyl cellulose is commercially available e.g. as powder or solution from Sigma Aldrich® or Dow Corning® and is commonly used as a thickener and/or emulsifier in various food and cosmetic products. According to the present invention, methylcellulose is present in a formulation comprising 30% dimeticone silica by mass such as Dow Corning® Medical Antifoam C.

An "ethylene oxide (EO)/propylene oxide (PO) copolymer" as referred to herein relates to block copolymers based on ethylene oxide and propylene oxide. EO/PO copolymers are known in the art and have been described as having demulsifying and de-foaming capabilities. Several EO/PO copolymers are commercially available, for example from Dow Corning Corp. under the trademark TERGITOL™ and from BASF Corporation under the trademark PLURONIC®.

According to the present invention, the concentration of the foam-suppressing and/or foam-destroying substance in the solution is, preferably, less than or equal to 0.05% (m/v). Preferably, the foam-suppressing and/or foam-destroying substance is added to the solution in a range of about 0.01 to 0.5 g/L. Preferably, an alkoxylated fatty acid ester on a vegetable basis formulated as a liquid with a density of 1000 kg/m$^3$ and a dynamic viscosity of 500 mPa·s such as Struktol® J673/J673A is added to the solution in a range of about 0.01 to 0.4 g/L. More preferably, an alkoxylated fatty acid ester on a vegetable basis formulated as a liquid with a density of 1000 kg/m3 and a dynamic viscosity of 500 mPa·s such as Struktol® J673/J673A is added at a concentration of at least 0.15 g/L. An emulsion comprising 30% dimeticone silica by mass and methylcellulose such as Dow Corning® Medical Antifoam C, is preferably added to the solution in a range of about 0.01 to 0.5 g/L. More preferably, an emulsion comprising 30% dimeticone silica by mass and methylcellulose such as Dow Corning® Medical Antifoam C, is added to the solution in a concentration of about 0.5 g/L. A silicone emulsion comprising 30% food-grade silicone having a pH of 3.5 such as Xiameter® AFE 0100 is preferably added to the solution in a range of about 0.025 to 0.5 g/L. More preferably, A silicone emulsion comprising 30% food-grade silicone having a pH of 3.5 such as Xiameter® AFE 0100 is added to the solution in a concentration of about 0.5 g/L.

In a preferred embodiment of the present invention, the foam-suppressing and/or foam-destroying substance shall be directly added to the color-imparting reagent of the color-turnover-based protein quantification method as explained elsewhere herein. Preferably, the foam-suppressing and/or foam-destroying substance is added to the color-imparting reagent in a concentration of about 0.05% (m/v). It is envisaged that the color-imparting reagent comprising the foam-suppressing and/or foam-destroying substance can be stored for several days, weeks, months or even years at an appropriate temperature (e.g. at 4 degrees) and place (light-protected) and applied as "ready-to-use solution" when performing the color-turnover-based protein quantification method, e.g. the Bradford assay.

Also preferably, the foam-suppressing and or foam-destroying substance according to the present invention leaves no relevant residues on surfaces such as cuvettes, microtiter plates or glass ware. Relevant as used in this context means that no residues are present that significantly influence the measurement result.

Determining the amount of a protein can be done by various means and methods known to those skilled in the art. According to the present invention, the amount of the one or more protein(s) is to be determined in the second solution as explained elsewhere herein. Preferably, the amount of the one or more protein(s) in the second solution shall be determined within a time window of 0 minutes to 2 hours, 0 minutes to 1.5 hours, 0 minutes to 1 hour, 0 minutes to 30 minutes, 2 minutes to 30 minutes, 5 minutes to 30 minutes or 10 minutes to 30 minutes. More preferably, the determination of the protein amount, i.e. the readout of the protein quantification assay in the second solution, takes place within a period of less than 30 minutes, less than 20 minutes, less than 15 minutes, less than 10 minutes, less than 5 minutes, less than 2 minutes after the addition of the at least one foam-suppressing and/or foam-destroying substance. Most preferably, the determination of the amount of the one or more protein(s) in the second solution takes place within a period of less than 30 minutes after the addition of the at least one foam-suppressing and/or foam-destroying substance. Even more preferred, the determination takes place within a period of less than 30 minutes and more than 10 minutes after the addition of the at least one foam-suppressing and/or foam-destroying substance. It will be understood, that the foam-suppressing and/or foam-destroying substance may be added directly to the first solution resulting in a second solution or may be first added to a color-imparting reagent that then is added to the first solution resulting in a second solution as explained elsewhere herein in detail.

Means and methods for quantifying proteins are well known in the art and include, for example, color-turnover-based protein quantification methods such as the Bradford protein assay, the BCA protein assay or the Lowry protein assay and non-color-turnover-based protein quantification method such as the Edelhoch-Method or UV spectroscopy. It is understood by those skilled in the art that different techniques may differ in their sensitivity as well as their susceptibility to disturbances, e.g. bubble formation in the measurement sample.

In a color-turnover-based protein quantification method or colorimetric test, the discoloration of the protein solution is typically investigated after adding a certain dye or color-imparting reagent to the protein solution and then compared to the discoloration of a calibration solution with a known protein concentration. In a preferred embodiment of the present invention the color-turnover-based protein quantification method is selected from the group consisting of: Bradford assay, BCA assay, Lowry assay and Sypro Ruby assay. Most preferably, the color-turnover-based protein quantification method is the Bradford Assay.

The Bradford assay, Bradford method or Bradford protein quantification is a spectroscopic analytical procedure used to measure the concentration of one or more protein(s) in a solution. It is based on an absorbance shift of the dye Coomassie Brilliant Blue G-250, which forms blue complexes with proteins, especially by interactions with arginine residues. Thereby the blue form of the Coomassie dye is stabilized. These complexes have an absorption maximum at a wavelength of 595 nm. Since the absolute level of absorption of the complexes is directly proportional to the protein concentration in the measured solution, protein quantities can be determined by reference to standard solutions, for example bovine serum albumin (BSA) solutions with known protein content.

The biuret test, also known as Piotrowski's test, can be used for detecting the presence of peptide bonds. In the presence of peptides, Cu+ forms violet-colored coordination complexes in an alkaline solution. It is known to those skilled in the art that the bicinchoninic acid (BCA) assay and the Lowry Method are modified variants of the biuret test.

The bicinchoninic acid (BCA) assay is based on the fact that cysteine/cystine, tyrosine, tryptophan and peptide bonds reduce Cu2+ to Cu+ under appropriate conditions. Cu+ forms a deep purple color complex which absorbs around 562 nm.

The Lowry assay or Lowry method is also a colorimetric method for the determination of protein concentrations in solutions, which is related to the biuret reaction. In the Lowry method Cu+ is oxidized back to Cu2+ by use of the so called Folin-Ciocalteu's reagent. In the first step, a copper-protein complex is formed in alkaline solution. This complex then reduces an added mixture of phosphomolybdate and phosphotungstate (Folin-Ciocalteu's reagent). Depending on the amount of proteins present, the solution becomes intensely blue. The absorption of the solution can then be measured at a wavelength of 540, 650 or 750 nm, and the protein quantities contained therein can be determined with the aid of a calibration curve.

The use of fluorescence, phosphorescent or luminescent means to quantify a protein of interest is a further preferred method. This includes the quantification of naturally occurring unmodified fluorescent proteins, modified proteins that have been labelled with fluorescent dyes such as Sypro® Ruby or Quant-iT™ dyes, or recombinantly expressed proteins comprising a fluorescent tag such as GFP, YFP, RFP or fusion proteins comprising GFP or luciferase, and the like, as explained elsewhere herein.

SYPRO® Ruby stains are new, luminescent metal chelate protein stains from Molecular Probes. The dyes are maximally excited at 470 nm and the emission peak is about 610 nm. SYPRO® Ruby was shown to selectively to basic amino acids of proteins, but not to DNA. The absorption maxima are 280 nm and 450 nm wave-length, the emission is maximum is at 610 nm wavelength. The "Sypro Ruby assay" according to the present invention relies on the SYPRO® Ruby dye for protein quantification.

Non-color-turnover-based protein quantification methods or non-colorimetic tests include the Edelhoch-Method or UV spectroscopy. These methods are based on the fact that the absorbance of a protein at 280 nm depends on the composition of the amino acids of a protein.

UV spectroscopy measures the so called UV range, i.e. electromagnetic radiation with a wavelength from 10 nm up to 400 nm which is a shorter wavelength than that of visible light. Typically, the absorption of a protein-containing aqueous solution is measured at 280 nm using a spectrophotometer. However, the determination of the protein concentration by UV spectroscopy requires that the protein(s) contain aromatic amino acids such as tyrosine (Y), phenylalanine (F) and/or tryptophan (W).

The Edelhoch method is a method for protein quantification on the basis of the average molar extinction coefficients for tryptophan, tyrosine and Cys—S—S—Cys (cysteine, disulfide bonds). Thus, the absorbance of a protein at 280 nm according to Edelhoch et al. (Edelhoch, H., 1967, Spectroscopic determination of tryptophan and tyrosine in proteins. Biochemistry, 6, 1948 1954) depends on its content of Trp (W), Tyr (T), and Cysteine (C).

The term "automated" as used herein refers to a method according to the present invention where at least one of steps a) to c) is automated. Means and methods for the automatization of biological assays are known to those skilled in the art and include, for example, the use of liquid handling stations. Preferably, a liquid handling station such as the JANUS™ automated workstation (PerkinElmer) in combination with a multimode plate reader such as the EnSpire Multimode Plate Reader (PerkinElmer) shall be used.

Also preferably, microtiter plates shall be used. The term "microtiter plate" as used herein includes all possible microtiter plate formats, for example mono-block-plates, 6-well, 12-well, 24-well, 96-well, 384-well and 692well plates and the like. More preferably, 96-well or 384-well, most preferably 96-well plates shall be used according to the present invention.

Advantageously, it has been found in accordance with the studies underlying the present invention that the addition of foam-suppressing and/or foam-destroying substances in a protein quantification assay helps to avoid readout problems and ensures the accuracy of the measurement results. Especially in the case of the parallelized and automated high throughput protein quantifications such as Bradford Assay, bubble formation at the liquid surface occurs due to pipetting and mixing in the automated working stations. The addition of foam-suppressing and/or foam-destroying substances according to the present invention helps to overcome this problem. In particular, anti-foam substances comprising an alkoxylated fatty acid ester on a vegetable basis formulated as a liquid with a density of 1000 kg/m3 and a dynamic viscosity of 500 mPa·s such as Struktol® J673/J673A, an emulsion comprising 30% dimeticone silica by mass and methylcellulose such as Dow Corning® Medical Antifoam C, and a silicone emulsion comprising 30% food-grade silicone having a pH of 3.5 such as Xiameter® AFE 0100 proved to be very suitable. These agents could be used at low concentrations making their high throughput use very cost-effective. Moreover, they substantially improved the accuracy and repeatability of the protein quantification measurements. In addition, no relevant residues on surfaces such as cuvettes or microtiterplates were observed, making them highly suitable for high throughput protein quantification methods such as an automated, parallelized Bradford assay. In summary, an optimized method for protein quantification is provided that fulfills the requirements of practicability, repeatability and reproducibility of the results, especially for parallelized and automated high throughput colorimetric protein quantification assays.

The above explanations and definitions of the terms apply throughout the specification. Moreover, in the following, typical embodiments of the composition according to the present invention are listed.

In a preferred embodiment of the method, the at least first solution is an aqueous solution or an extract.

In a further preferred embodiment of the method, the at least one foam-suppressing and/or foam-destroying substance comprises an alkoxylated fatty acid ester and/or a siloxane-based compound and/or methyl cellulose and/or an ethylene oxide (EO)/propylene oxide (PO) copolymer.

In yet a preferred embodiment of the method, the at least one foam-suppressing and/or foam-destroying substance is selected form the group consisting of: an alkoxylated fatty acid ester on a vegetable basis formulated as a liquid with a density of 1000 kg/m3 and a dynamic viscosity of 500 mPa·s, an emulsion comprising 30% dimeticone silica by mass and methylcellulose , and a silicone emulsion comprising 30% food-grade silicone having a pH of 3.5 .

In a preferred embodiment of the method, the concentration of the at least one foam-suppressing and/or foam-destroying substance in the solution is less than or equal to 0.05% (m/v).

In yet a preferred embodiment of the method, the protein concentration is determined by a non-color-turnover-based protein quantification method.

In yet a preferred embodiment of the method, the protein concentration is determined by a color-turnover-based protein quantification method.

In yet a preferred embodiment of the method, the color-turnover-based protein quantification method comprises the step of adding a color-imparting reagent and, optionally, wherein the least one foam-suppressing and/or foam-destroying substance is directly added to the color-imparting reagent.

In yet a preferred embodiment of the method, the color-turnover-based protein the color-turnover-based protein quantification method is selected from the group consisting of: Bradford assay, BCA assay, Lowry assay and Sypro Ruby assay.

In yet a preferred embodiment of the method, determining the amount of the one or more protein(s) in the second solution in step c takes place within a period of less than 30 minutes after the addition of the at least one foam-suppressing and/or foam-destroying substance.

In yet a preferred embodiment of the method, the at least one foam-suppressing and/or foam-destroying substance leaves no relevant residues on surfaces.

In yet a preferred embodiment of the method, step (a) and/or the step (b) and/or the step (c) is done in a microtiter plate.

In yet a preferred embodiment of the method, at least one of steps (a) to (c) is automated.

The present invention also encompasses the use of a foam-suppressing and/or foam-destroying substance ex vivo for the quantification of the protein content in a solution. Preferably, said foam-suppressing and/or foam-destroying substance is selected from the group consisting of: an alkoxylated fatty acid ester on a vegetable basis formulated as a liquid with a density of 1000 kg/m3 and a dynamic viscosity of 500 mPa·s, an emulsion comprising 30% dimeticone silica by mass and methylcellulose, and a silicone emulsion comprising 30% food-grade silicone having a pH of 3.5.

All references cited in this specification are herewith incorporated by reference with respect to their entire disclosure content and the disclosure content specifically mentioned in this specification. Full citations of the references are to be found elsewhere herein.

FIGURES

FIG. 1: Effect of the Struktol concentration (Struktol J673) on absorption over time. As the Struktol concentration increases, the absorption increases. An increase in absorption can be observed over time, and a saturation curve can be seen at lower Struktol concentrations up to approx. 0.2 g L−1, above that the course is linear.

Figure 2:
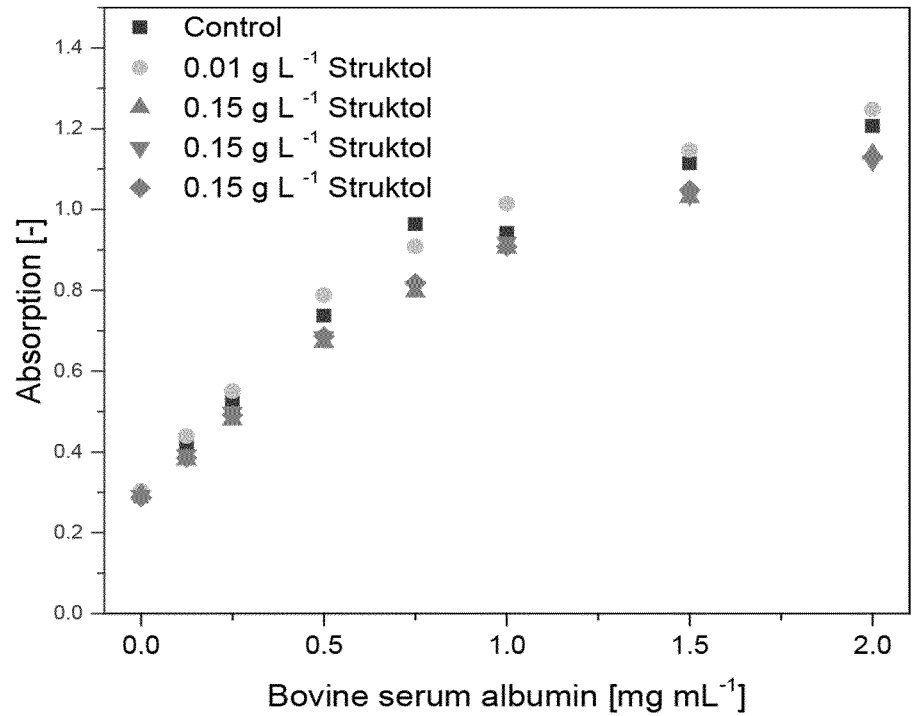
FIG. 2 shows absorption at various BSA/protein concentrations as well as anti-foam agent concentrations. Square: Control series without addition of anti-foam agent. A) Absorption of various Bradford-Reagent-Struktol J673-mixtures at ascending BSA concentrations. B) Absorption of various Bradford-Reagent-Xiameter AFE 0100-mixtures at ascending BSA concentrations. C) Absorption of 0.05 g of L−1 Xiameter AFE 0100 in Bradford Reagent for various proteins and ascending protein concentrations: the proteins BSA, RuBisCO (RuB) and Lysozyme (Lys) were tested. D) Absorption of various Bradford-Reagents-Medical Antifoam C (MAC)-mixtures at ascending BSA concentrations.
Figure 2:
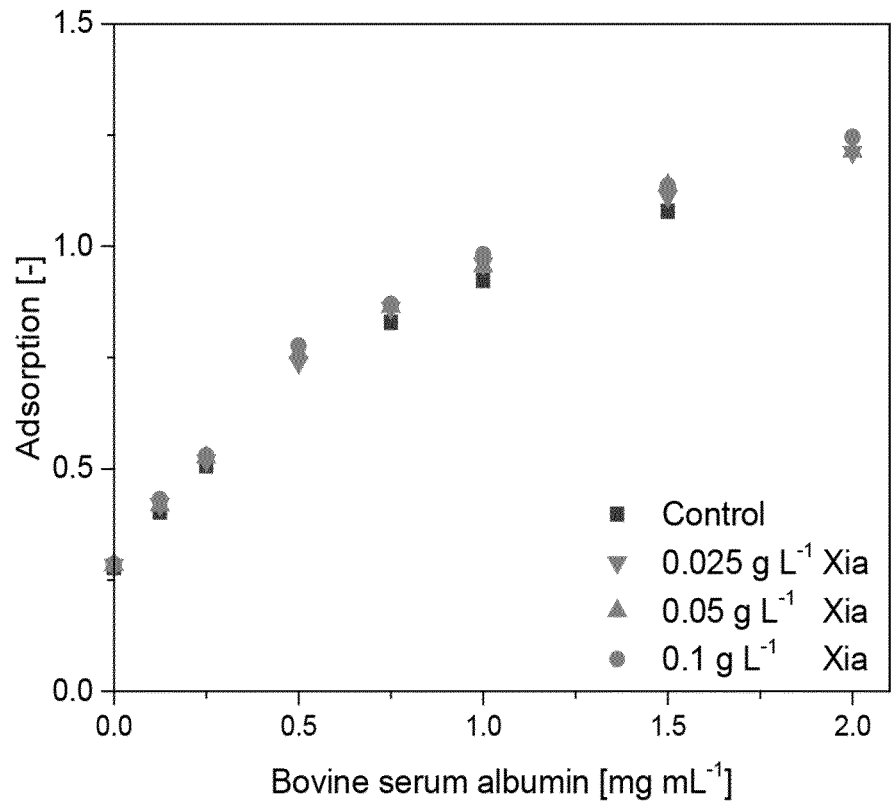

FIG. 2: Absorption at various BSA/protein concentrations as well as anti-foam agent concentrations. Square: Control series without addition of anti-foam agent. A) Absorption of various Bradford-Reagent-Struktol J673-mixtures at ascending BSA concentrations. B) Absorption of various Bradford-Reagent-Xiameter AFE 0100-mixtures at ascending BSA concentrations. C) Absorption of 0.05 g of L−1 Xiameter AFE 0100 in Bradford Reagent for various proteins and ascending protein concentrations: the proteins BSA, RuBisCO (RuB) and Lysozyme (Lys) were tested. D) Absorption of various Bradford-Reagents-Medical Antifoam C (MAC)-mixtures at ascending BSA concentrations.

Figure 3:
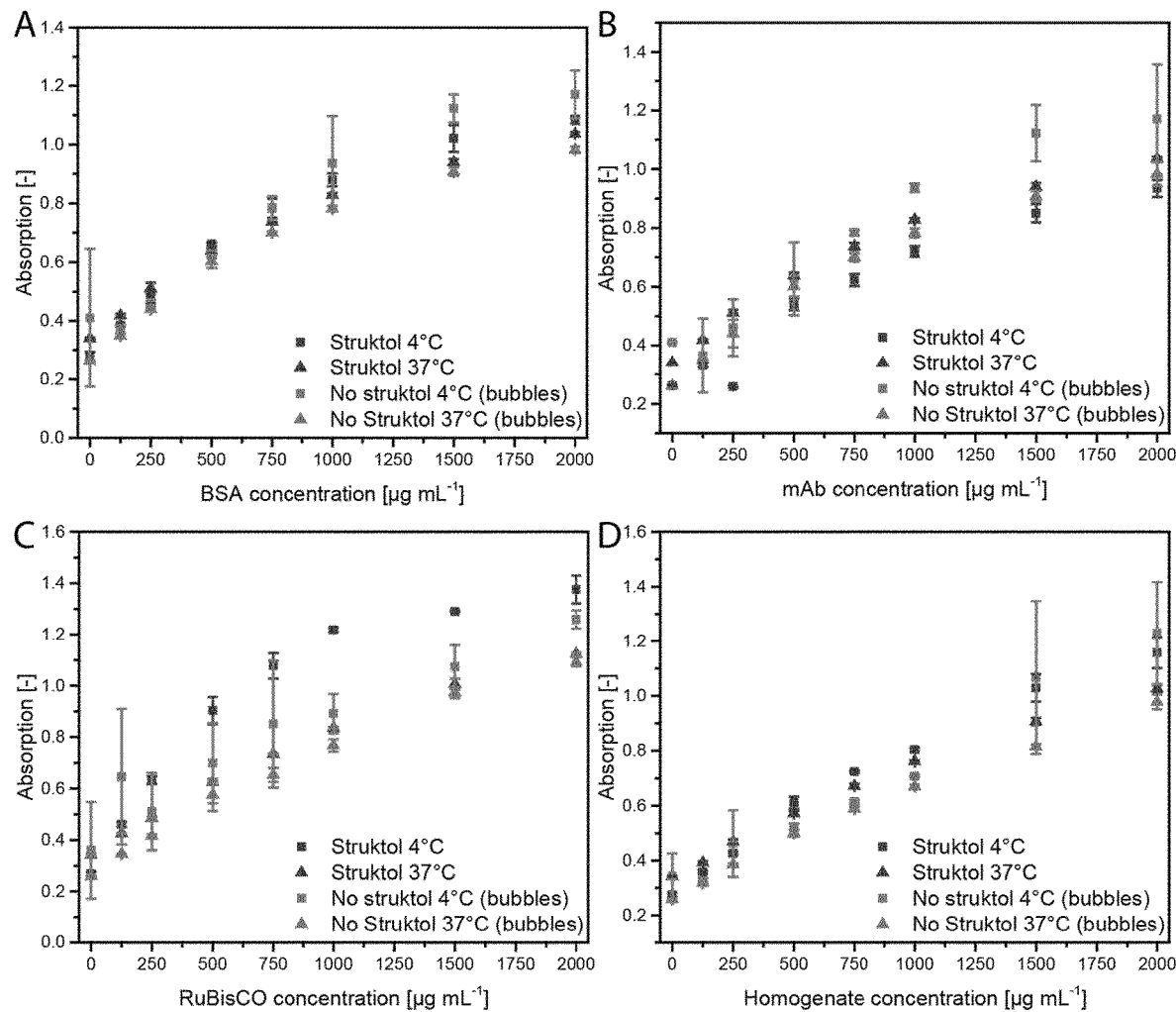
FIG. 3 shows absorption of Bradford solutions containing 0.15 g L−1 Struktol J673A or the equivalent amount of water mixed with A: Bovine serum albumin (BSA), B: Human anti-D immunoglobulin (mAb) and C: Ribulose-1,5-bisphosphat-carboxylase/-oxygenase (RuBisCO) or D: tobacco homogenate at protein concentrations from 0-2000 μg mL−1.

FIG. 3: Absorption of Bradford solutions containing 0.15 g L−1 Struktol J673A or the equivalent amount of water mixed with A: Bovine serum albumin (BSA), B: Human anti-D immunoglobulin (mAb) and C: Ribulose-1,5-bisphosphat-carboxylase/-oxygenase (RuBisCO) or D: tobacco homogenate at protein concentrations from 0-2000 μg mL−1.

Figure 4:
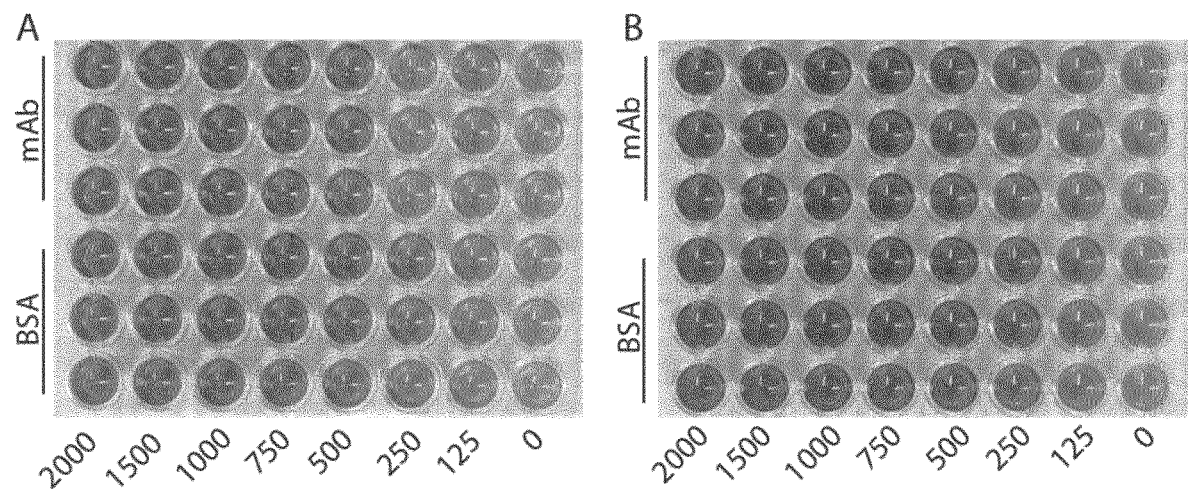
FIG. 4 shows Bradford test of BSA and mAB from 0-2000 mg mL−1 using solution with Struktol J673A stored at 4° C. (A) and at 37° (B).

FIG. 4: Bradford test of BSA and mAB from 0-2000 mg mL−1 using solution with Struktol J673A stored at 4° C. (A) and at 37° (B).

Figure 5:
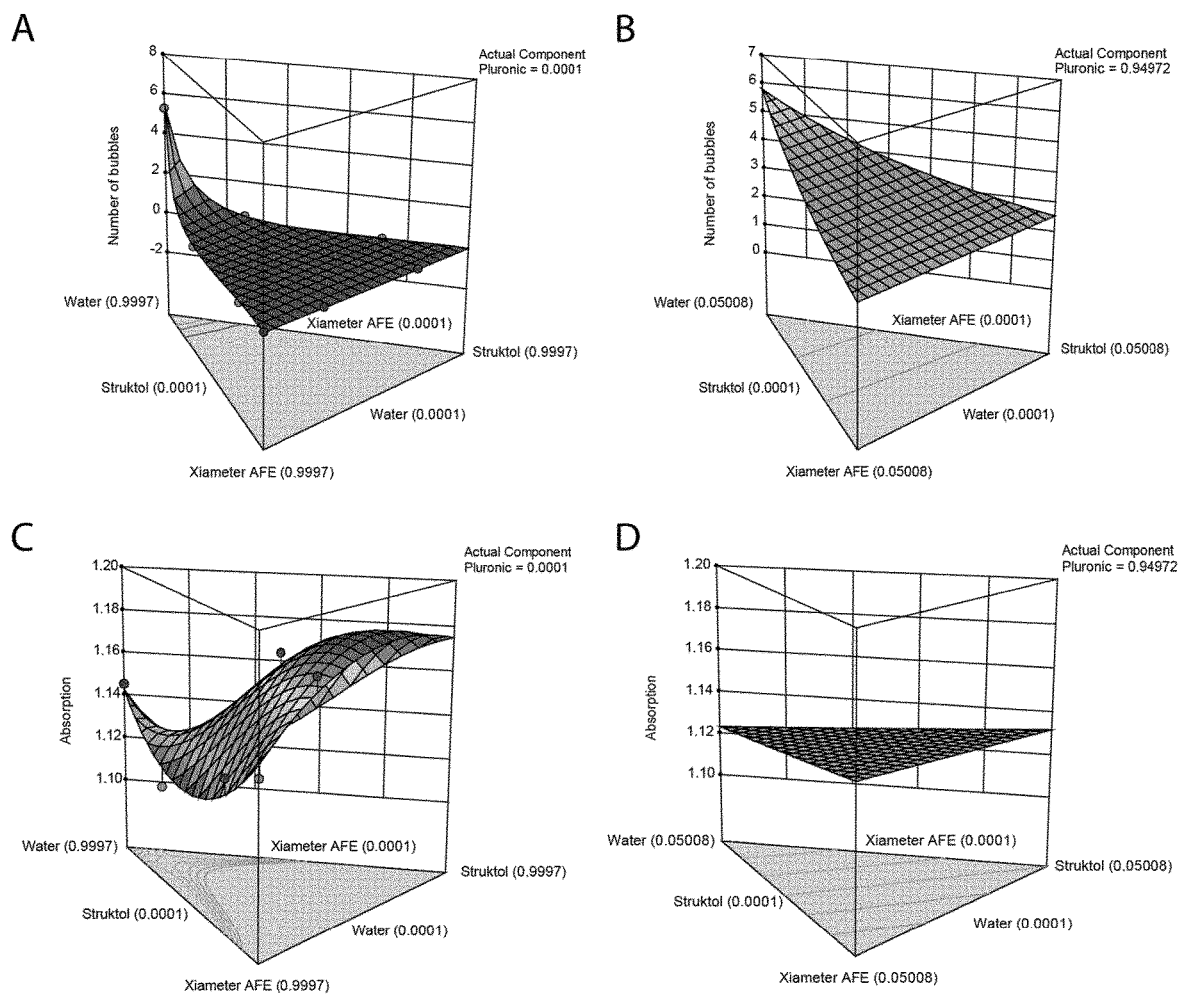
FIG. 5 shows influence of different antifoam agent mixtures on the number of bubbles and the total absorption. A: Number of Bubbles at lowest Pluronic L61 concentration. B Number of Bubbles at highest Pluronic L61 concentration. C: Absorption at lowest Pluronic concentration. D: Absorption at highest Pluronic concentration.

FIG. 5: Influence of different antifoam agent mixtures on the number of bubbles and the total absorption. A: Number of Bubbles at lowest Pluronic L61 concentration. B Number of Bubbles at highest Pluronic L61 concentration. C: Absorption at lowest Pluronic concentration. D: Absorption at highest Pluronic concentration.

EXAMPLES

Example 1: Testing of Different Foam-Suppressing and/or Foam-Destroying Substances To overcome the problem of foaming in a protein quantification assay, different foam-suppressing and/or foam-destroying substances were tested in a Bradford Protein assay. The following substances were tested: Anti-foam agents comprising an alkoxylated fatty acid ester such as Struktol J673, Struktol J673 A, Struktol J647, silicone-based anti-foam agents such as Medical Antifoam C and Xiameter AFE 0100 as well as bifunctional blockpolymers such as Pluronic L61 and BisomerG30. Detailed information on the materials and instruments used can be found below.

Materials:
Anti-foam agents: Struktol J673, Struktol J673 A, Struktol J647, Dow Corning Medical Antifoam C, Xiameter AFE 0100, Pluronic L61, BisomerG30

Color-imparting reagent for the protein assay: Bradford-Reagent, taken from Pierce Coomassie Protein Assay Kit (ThermoFisher Scientific)

Proteins: BSA-Standard, taken from Pierce Coomassie Protein Assay Kit (ThermoFisher Scientific), RuBisCO purified from *Nicotiana tabacum* SR1, Lysozyme (Sigma Aldrich)

Microtiter plates (96 Well)

BioPhotometer (Eppendorf)

Plate Reader Enspire (PerkinElmer)

Pipetting robot JANUS automated workstation (PerkinElmer)

Determination of Defoaming Capacity:

To determine the defoaming capacity of the above mentioned substances, the Bradford Reagent was used and the extinction of the reagent was determined. A 100 g L$^{-1}$ solution was first prepared from all anti-foam agents. Starting from this solution, working solutions with concentrations between 1.00-0.01 g L$^{-1}$ were established. In a first step, each anti-foam agent was added at different concentrations to the Bradford Reagent (final volume: 5 ml). Afterwards, the Bradford Reagent and the anti-foam agent were mixed by shaking and the time—until a complete reduction of the bubbles was seen—was measured. This was repeated after 30 and 60 minutes. The extinction of the mixture was measured at the beginning and at the end and compared with the reference (5 mL pure Bradford-Reagent).

Results:

Struktol J673 and J673A showed fast bubble reduction (>1 min at 0.01 g $L^{-1}$)

Dow Corning Medical Antifoam C and Xiameter AFE 0100 showed fast bubble reduction (>1 min at 0.01 g $L^{-1}$)

The dissolving capacity of Struktol J647 in aqueous solutions was not as satisfying as for Struktol J673 and J673A Pluronic L61 and Bisomer G30 showed middle bubble reduction (>5 min at 1 g $L^{-1}$)

In summary, Struktol J673 and J673A, Dow Corning Medical Antifoam C and Xiameter AFE 0100 showed the best results in terms solubility and efficient bubble reduction.

Absorption in Dependence on the Concentration of the Anti-Foam Reagent Over Time:

Struktol J673 was further used to investigate the adsorption in dependence of the concentration of the anti-foam reagent over time. To this end, 900 µL of the pure Bradford reagent (control) and of different test solutions (containing the Bradford reagent and Struktol J673 in different concentrations) were mixed, followed by extinction measurements in cuvettes at 595 nm using a photometer. The cuvettes were stored in a light protected environment at room temperature and the measurements (using the same solutions and cuvettes) were repeated after 5, 10, 15, 20 and 60 minutes.

As can be seen in FIG. 1, the absorption increases as the Struktol concentration increases. An increase in absorption can be observed over time, and a saturation curve can be seen at lower Struktol concentrations up to approx. 0.2 g $L^{-1}$, above that the course is linear.

Inhibition of Bubble Formation is Dependent on the Concentration of the Anti-Foam Agent A series of aqueous solutions comprising increasing BSA concentrations ranging from 0 to 2000 µg $mL^{-1}$ and different anti-foam solutions were mixed. After an incubation period of 10 minutes, the bubble formation was examined The absorption at various BSA/protein concentrations as well as anti-foam agent concentrations can be seen in FIG. 2. Medical Antifoam C, Xiameter AFE 0100, Struktol J673 and Struktol J673A showed an effective bubble reduction already at very low concentrations, and worked best at concentrations around 0.5 g $L^{-1}$.

Example 2: Stability and Mixing Experiments

Stability

The long-term stability and performance of Bradford solution containing Struktol J673A was tested. To do so one batch of Bradford solution was divided in to four glass bottles. Two glass bottles were supplemented 0.15 g $L^{-1}$ Struktol J673A and the other two with the same amount of water. One with and one without Struktol J673 was stored 4° C. (recommended storage temperature of the manufacturer) for four weeks and the other two at 37° C.

After four weeks the solutions were used to perform a Bradford assay with three pure proteins (Bovine serum albumin (BSA), Human anti-D immunoglobulin (mAb) and Ribulose-1,5-bisphosphat-carboxylase/-oxygenase (RuBisCO)) and a protein mixture (tobacco homogenate) using triplicates for each protein concentration (FIG. 3).

After storage at 4° C., results show a distinct decrease of the standard deviation (in average 8.4 times lower) if Struktol J673 was added. This effect is lower after the storage at 37° C., here the standard deviation is only 2.6 times higher if no Struktol was added. In general the curve trends are comparable only the solution stored at 4° C. with Struktol J673A and mixed with RuBisCO show a higher absorption. The storage at 37° C. led to a color shift from brown to red-brown independent if Struktol J683A was added or not (FIG. 4). Therefore it was shown that Struktol has no negative effects on the Bradford assay after long-term storage independently on the storage temperature. Higher temperatures than 4° C. can change the color of the Bradford solution and therefore the recommended storage area by the manufacturer should be followed.

Mixing

We have already successfully tested three single antifoam agents (Struktol J673/J673A, Medical Antifoam C and Xiameter AFE) which prevented bubble formation effectively. Pluronic L61 was also tested but did not show effective bubbles disruption. Now we tested a mixture of water, Struktol J673A (alkoxylated fatty acid ester), Xiameter AFE 0100 (silicon) and Pluronic L61 (poloxamer) in order to see if the different chemical properties perform better in a mixture and can therefore be applied using lower concentrations. To do so Struktol and Xiameter AFE 0100 was mixed with Bradford solution using the previous determined concentrations (0.15 g $L^{-1}$ and 0.50 g $L^{-1}$, respectively) Pluronic L61 and water was mixed with Bradford solution using 0.5 g $L^{-1}$ for both. The prepared solutions were then mixed together according to the design of experiment (DoE) requirements.

Results show (FIG. 5B) that Pluronic L61 does not reduce the number of bubbles effectively in a mixture. The mixture of Struktol J673A and Xiameter AFE 0100 was effective at almost all tested mixtures, only if the content of the Bradford-water solution was higher than around 80% bubbles occurred (FIG. 5A+B). The amount of antifoam agent needed can be reduced by 92% in a mixture compared to using either Struktol J673 or Xiameter AFE 0100 alone with the Bradford solution. Struktol J673A led to a small increase of the absorption (FIG. 5C+D) of less than 8% and is therefore negligible. Since the mixture of two antifoam agents reduces the needed amount of the agents and still avoids bubbles, a mixture can be used in future applications.

What is claimed is:

1. A method for determining an amount of one or more proteins in a solution comprising:
    (a) providing at least a first solution that is known to contain or suspected of containing one or more protein(s),
    (b) mixing at least one foam-suppressing and/or foam-destroying substance comprising an alkoxylated fatty acid ester into the first solution, resulting in a second solution, wherein the second solution is a homogeneous mixture comprising the first solution and the alkoxylated fatty acid ester, and
    (c) determining the amount of the one or more protein(s) in the second solution.

2. The method of claim 1, wherein the at least first solution is an aqueous solution or an extract.

3. The method of claim 1, wherein the at least one foam-suppressing and/or foam-destroying substance further comprises a siloxane-based compound and/or methyl cellulose and/or an ethylene oxide (EO)/propylene oxide (PO) copolymer.

4. The method of claim 1, wherein the at least one foam-suppressing and/or foam-destroying substance is an alkoxylated fatty acid ester on a vegetable basis formulated as a liquid with a density of 1000 kg/m3 and a dynamic viscosity of 500mPa·s.

5. The method of claim 1, wherein a concentration of the at least one foam-suppressing and/or foam-destroying substance in the second solution is less than or equal to 0.05% (m/v).

6. The method of claim 1, wherein a protein concentration is determined by a non-color-turnover-based protein quantification method.

7. The method of claim 1, wherein a protein concentration is determined by a color-turnover-based protein quantification method.

8. The method of claim 7, wherein the color-turnover-based protein quantification method comprises a step of adding a color-imparting reagent to the second solution and, optionally, wherein the at least one foam-suppressing and/or foam-destroying substance is directly added to the color-imparting reagent before both the color-imparting reagent and the at least one foam-suppressing and/or foam-destroying substance are added to the first solution to form the second solution.

9. The method of claim 7, wherein the color-turnover-based protein quantification method is selected from the group consisting of: Bradford assay, BCA assay, Lowry assay and Sypro Ruby assay.

10. The method of claim 1, wherein determining the amount of the one or more protein(s) in the second solution in step c takes place within a period of less than 30 minutes after the addition of the at least one foam-suppressing and/or foam-destroying substance.

11. The method of claim 1, wherein the at least one foam-suppressing and/or foam-destroying substance leaves no relevant residues on surfaces.

12. The method of claim 1, wherein step (a) and/or step (b) and/or step (c) is done in a microtiter plate.

13. The method of claim 1, wherein at least one of steps (a) to (c) is automated.

14. The method of claim 1, wherein the at least one foam-suppressing and/or foam-destroying substance is mixed with a color-imparting reagent resulting in a mixture of the at least one foam-suppressing and/or foam-destroying substance and the color-imparting reagent prior to step (b), wherein step (b) comprises mixing the mixture of the at least one foam-suppressing and/or foam-destroying substance and the color-imparting reagent into the first solution.

* * * * *